United States Patent [19]
McCrory

[11] Patent Number: 5,171,226
[45] Date of Patent: Dec. 15, 1992

[54] METHOD OF LONG TERM EPIDURAL CATHERIZATION

[75] Inventor: Jennifer J. McCrory, Lincoln, R.I.

[73] Assignee: The Kendall Company, Mansfield, Mass.

[21] Appl. No.: 703,320

[22] Filed: May 20, 1991

[51] Int. Cl.⁵ .............................. A61M 5/178
[52] U.S. Cl. .................. 604/164; 128/898; 604/264; 604/53
[58] Field of Search ............ 604/158, 164, 264; 606/170, 185, 187; 128/898

[56] References Cited

U.S. PATENT DOCUMENTS

| | | | |
|---|---|---|---|
| 4,431,426 | 2/1984 | Groshong et al. | 604/164 |
| 4,432,752 | 2/1984 | Marlon | 604/164 |
| 4,453,928 | 6/1984 | Steiger | 604/164 |

Primary Examiner—C. Fred Rosenbaum
Assistant Examiner—William W. Lewis
Attorney, Agent, or Firm—Alvin Isaacs

[57] ABSTRACT

A novel subcutaneous tunneling device is disclosed which is particularly directed to long-term epidural catheters for relieving intractable pain, which catheters require tunneling from the paravertebral incision where the catheter is introduced into the epidural space to a lateral location where administration of a narcotic is more conveniently handled. The tunneling device consists essentially of a hollow shaft having a solid removable cutting tip on one end thereof. Following removal of the solid cutting tip, a catheter, cannula or other tubular article may then be passed through the shaft.

3 Claims, 1 Drawing Sheet

METHOD OF LONG TERM EPIDURAL CATHERIZATION

BACKGROUND OF THE INVENTION

Medical/surgical procedures requiring the step of tunneling subcutaneously between two locations for administration of a fluid to a patient are well known in the art.

Illustrative of such procedures is the relatively recent advancement in relieving intractable pain, e.g. in terminal cancer patients, by long-term epidural catheterization. In such procedures, an epidural catheter for administering a narcotic such as morphine extends subcutaneously from the paravertebral entry site where the catheter is introduced into the epidural space to an exit site on the flank where it is attached to a syringe or other source of narcotic to be introduced into the epidural space for pain management.

The tunneling step may be performed from the exit site for connecting the external portion of the catheter to the drug source toward the paravertebral entry site of the epidural catheter or, alternatively, it may be performed from the entry site to the desired exit site.

In either case, the tunneling device should not only be of sufficient length to provide a subcutaneous passageway between the two points in a single pass, but it must also be malleable so as to be capable to being shaped to conform to the shape of the body between these two points before tunneling is commenced.

To illustrate the state of the art pertaining to long-term epidural catheters, mention may be made of the Du Pen(TM) Long-Term Epidural Catheter commercially available from Davol, Inc., a subsidiary of C. R. Bard, Inc.

The Du Pen catheter system consists of three component parts: (1) an epidural catheter segment placed through a needle into the epidural space; (2) an exteriorized line equipped with an external luer connection and a subcutaneous Dacron cuff; and (3) a small splice segment to join the two catheter segments.

In view of the luer connection and cuff, it will be readily understood that the tunneling step must be from the exit site on the flank, e.g. from a subcostal location on the mid-nipple line toward the paravertebral incision provided for introducing the epidural catheter segment.

To accomplish subcutaneous tunneling procedures of the foregoing brief description, essentially two types of tunneling devices have heretofore been employed: (1) a solid tunneler of metal or plastic in which one end of the catheter to be tunneled is slipped over the trailing end of the tunneler (the end opposed from the leading end having the cutting tip) and then dragged through the passageway created by the tunneler; or (2) a hollow tunneler open at the trailing end and having an opening in the cutting tip of sufficient diameter to permit passage of the catheter therethrough, in which case after the tunnel is made and with the tunneler still in place, the catheter may then be threaded through the opening in the tip and out the trailing end of the hollow tumbler.

While either type of these malleable tunnelers is quite satisfactory most of the time, each does nevertheless possess inherent properties which may adversely affect the tunneling step.

Since the solid tunneler functions by dragging the catheter behind it through the passageway created by tunneling, it follows that the catheter is dragged through the debris of host origin caused by the tunneler. This may, in turn, cause certain problems requiring the tunneling and, in some instances the insertion of the epidural catheter itself to be repeated. First, kinking of the catheter may be caused. Secondly, any undue or sudden resistance in the advancement of the catheter behind the tunneler may cause the catheter to slip off the trailing end of the tunneler. Finally, if the epidural catheter is the component to be tunneled (as will be the case in the preferred long-term epidural catheter system contemplated for use with the present invention and which will be discussed in more detail hereinafter), any such resistance may cause the distal end of the epidural catheter to become dislodged from its position within the epidural space. Such dislodgement may or may not require the catheter to be removed and re-introduced into the epidural space, depending upon the extent of the dislodgement.

The second type of tunneling device heretofore used, namely the hollow tunneler having an opening in the cutting tip, does not suffer from the inherent dangers noted above. However, it may instead cause different problems.

Since the cutting tip at the leading end of the tunneler has an opening permitting passage of the catheter therethrough, there is a tendency for flesh, blood and/or other debris from the tunneling to enter the hollow tunneler through this opening at the leading end. This in turn may at least partially clog up the passageway within the tunneler, notably at the leading end, thereby impairing threading the catheter therethrough and possibly causing kinking within the tunneler. Additionally, some of this debris of host origin may enter the leading end of the catheter, thus providing an environment for infection due to bacterial contamination.

Stated simply, the task of the present invention is to provide a subcutaneous tunneling device which obviates the aforementioned inherent dangers when employing the tunnelers of the prior art, thereby providing a consistently efficacious device for accomplishing subcutaneous tunneling between two sites for the pain management or other medical procedure contemplated.

BRIEF DESCRIPTION OF THE INVENTION

In accordance with the present invention, this task is solved in an elegant manner by providing a malleable tunneler consisting of a hollow shaft having a solid cutting tip releasably secured to one end thereof, e.g. by threading. After tunneling, the tip is removed and the catheter then passed through the hollow shaft.

DETAILED DESCRIPTION OF THE INVENTION

Figure 1:
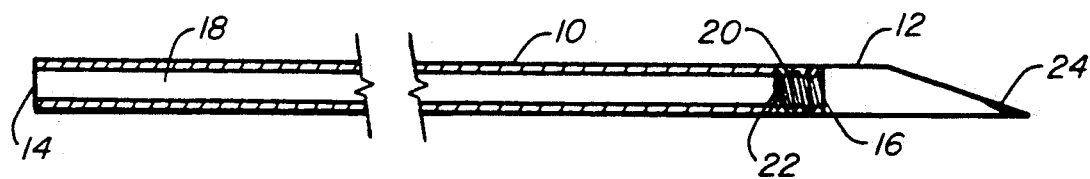
FIG. 1 is a longitudinal sectional view illustrating a preferred from of the hollow tunneler of this invention.
Figure 2:
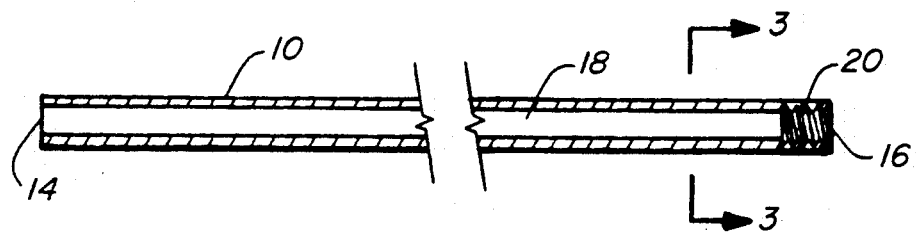
FIG. 2 is a similar view of the shaft member of the device of FIG. 1.
Figure 3:
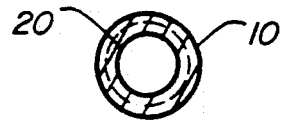
FIG. 3 is an enlarged cross-sectional view taken along lines 3—3 of FIG. 2.
Figure 4:
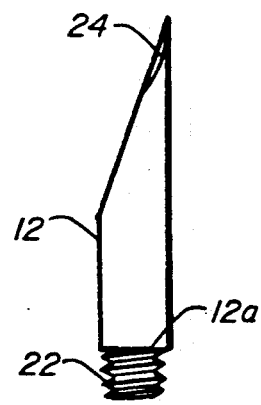
FIG. 4 is a longitudinal view of the solid cutting tip of the device of FIG. 1.

As was heretofore mentioned, the present invention is directed to a subcutaneous tunneling device, which device finds particular use in the preparation of long-term epidural catheters which may be considered as having a distal internal end inserted dorsally into the epidural space and an external proximal end extending through the skin at a location on the flank of the patient where it can be more conveniently attached to a syringe or other source of the liquid drug to be administered epidurally.

The novel tunneling device of this invention will be readily understood by reference to the accompanying drawing.

As shown herein, the tunneling device of this invention consists essentially of a hollow shaft 10 and a solid cutting tip 12. Shaft 10 defines a chamber 18 extending between opposed ends 14, 16 of the shaft. In its preferred form, shaft 10 is tapped or contains internal threads 20 adjacent end 16. Solid cutting tip 12 has external threads 22 at its base 12a to mate with the internal threads 20 of hollow shaft 10 so that the respective elements 10, 12 can be screwed together for tunneling and thereafter readily separated by unscrewing. As shown, tip 12 is preferably beveled or chamfered at its cutting end 24.

While mating of the threads so the respective elements may releasably engage one another is the preferred means, it will be appreciated that the invention is not restricted thereto and other means for doing so will be readily suggested to those skilled in the art. By way of illustration, they may releasably engage one another for tunneling by a friction fit wherein the base 12a of the cutting tip fits within end 16 of shaft 10.

As was alluded to previously, the tunneler must be malleable. In this context, it may be made of a suitable medical grade semi-rigid vinyl or other plastic material. However, a metal such as stainless steel is preferred.

It will be appreciated that the dimensions of the tunneler may vary in accordance with the contemplated usage and are accordingly not capable of precise quantification. In general, the tunneler should of course be of sufficient length to traverse the whole area to be tunneled in a single pass. Likewise, the diameter of the tunneler must be sufficiently large to present a passage for the catheter, cannula or other tubular article to be tunneled subcutaneously.

By way of illustration, the preferred long-term epidural catheter for relieving intractable pain contemplated to be provided by the novel tunneling device of this invention is that described and claimed in Applicant's concurrently filed copending application Ser. No. 703,321.

As is disclosed therein, an epidural catheter of one-piece construction is provided extending from the paravertebral entry point subcutaneously to the exit site, in combination with a protective enforcement sleeve adapted to be tunneled subcutaneously within the exit site for a short distance over the proximal end portion of the catheter. The proximal end of the sleeve is permanently attached to a catheter connector having a luer fitting for securing the catheter in fluid communication via the connector to the source of liquid drug to be administered epidurally. After the catheter is tunneled through the skin and out the exit site, the tunneler is removed. Thereafter, the distal or free end of the sleeve is then inserted over the free proximal end of the catheter and then part way into the passage created by the tunneler. After securing the catheter to the catheter connector and closing both the entry and exit sites in the skin with sutures and sterile dressings, the system is then ready for use.

With the novel long-term epidural catheter system described and claimed in the aforementioned copending application, the epidural catheter may for example be a 20 gauge (0.036 inch) and the protective sleeve may have an outer diameter of on the order of 0.144 inch (11 French). A tunneler in accordance with the present invention intended to be used with a catheter system of these general dimensions may, for purposes of further illustration, be on the order of 10-12 inches in length and possess an inner diameter of at least 0.06 inch and an outer diameter of at least the same size as the sleeve, i.e. 0.144 inch.

The following description is illustrative of the preparation of a patient for intractable pain relief utilizing the long-term epidural catheter of the aforementioned copending application in combination with the tunneler of the present invention.

The epidural catheter is first threaded through a needle into the epidural space in per se known manner. With the needle still in place to avoid inadvertent damage to the catheter, a small incision is made with a scalpel extending cranially and caudally approximately 0.5-1.0 cm. All tissue is dissected away from the needle to allow the catheter to fall freely into the incision as the tunneler is later advanced. The epidural needle is then removed. If a wire stylet is used for insertion of the catheter, it is also removed.

The malleable tunneler of the present invention is then manually shaped to match the contour of the flank. The skin at the paramedial incision is lifted and the shaped tunneler is introduced subcutaneously and then guided laterally toward the contemplated exit site on the flank.

When the tip of the tunneler has reached the desired exit point laterally, the tunneler is turned away from the patient, thereby forcing the cutting tip up against the skin. A scalpel is then used to cut down to expose the tip, after which the tunneler is advanced through the thus provided exit site. Following advancement of the leading end of the tunneler through the skin, the tunneler tip 12 is removed and the catheter passed through the chamber or lumen 18 within hollow shaft 10 and out through end 16. Shaft 10 is then removed through the exit site.

Next, the protective sleeve (provided with a cuff of Dacron or other suitable material adjacent its proximal end portion) is advanced over the free proximal end of the catheter extending above the skin and down to the exit site. The skin is then lifted with forceps and the sleeve advanced through the exit site into the passage provided by the tunneler until the cuff is approximately two inches beneath the skin.

The epidural catheter may then be trimmed to fit within the adapter preattached to the sleeve and the adapter then moved to the closed position to secure the catheter.

Both the paramedical incision and ventral exit sites are then closed with suitable sutures and sterile dressings applied. After attaching a removable morphine filter/injection cap assembly, a saline solution may be injected to confirm the catheter integrity.

The long-term epidural catheter is then ready to commence introducing narcotic into the epidural space on an as-needed dosage for pain management.

From the foregoing description, it will thus be seen that the novel tunneling device of this invention protects the catheter from biological debris of host origin, kinking or other damage during the tunneling step from the paravertebral entry point to the exit site. Additionally, since it threads easily through the tunneler, there is no resistance or pulling which can cause the catheter to become dislodged from its placement within the epidural space, a problem noted previously in discussing the prior art solid tunnelers. Of course, it can't possibly become separated from the tunneler beneath the skin.

While reference has been made throughout the description to subcutaneous tunneling procedures for long-term epidural catheterization, it will be appreciated that the invention is not limited thereto and is applicable to any tunneling procedures where the cutting tip of the tunneler projects externally following tunneling so as to be removable. It may, for example, be used in tunneling procedures wherein a central venous catheter (CVC) is tunneled from a suitable exit sit, e.g. at the midline, toward the venous insertion site, e.g. the subclarian entry point where the CVC is to be introduced into the blood vessel.

Since certain changes may be made without departing from the scope of the invention herein contemplated, it is to be expressly understood that the foregoing description, including the drawing, is by way of illustration and not by way of limitation and the invention is limited only as indicated in the appended claims.

What is claimed is:

1. A method of providing long term epidural catherization comprising the steps of introducing a distal end of an epidural catheter into the epidural space at a first location; and thereafter tunneling the catheter to an exit site at another location where a proximal end of the catheter is placed in liquid communication with a liquid to be administered to the body through the catheter.

2. A method as defined in claim 1 including the steps of advancing tip of the tunneler through the skin, thereafter removing the tip from the shaft and then passing the catheter through the shaft of the tunneler.

3. A method as defined in claim 1 wherein the shaft is removed from the skin after the catheter has passed through the shaft so that one end of the catheter is above the skin at the exit site.

* * * * *